United States Patent
Lee et al.

(10) Patent No.: US 12,111,244 B2
(45) Date of Patent: Oct. 8, 2024

(54) METHOD FOR CALCULATING A DENSITY OF STEM CELLS IN A CELL IMAGE, ELECTRONIC DEVICE, AND STORAGE MEDIUM

(71) Applicant: HON HAI PRECISION INDUSTRY CO., LTD., New Taipei (TW)

(72) Inventors: Wan-Jhen Lee, New Taipei (TW); Chin-Pin Kuo, New Taipei (TW); Chih-Te Lu, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 421 days.

(21) Appl. No.: 17/523,989

(22) Filed: Nov. 11, 2021

(65) Prior Publication Data

US 2022/0178814 A1 Jun. 9, 2022

(30) Foreign Application Priority Data

Dec. 3, 2020 (CN) .......................... 202011416157.4

(51) Int. Cl.
*G06K 9/00* (2022.01)
*G01N 15/1433* (2024.01)
(Continued)

(52) U.S. Cl.
CPC ..... *G01N 15/1433* (2024.01); *G01N 33/4833* (2013.01); *G06T 7/0012* (2013.01);
(Continued)

(58) Field of Classification Search
CPC ........... G01N 15/1433; G01N 33/4833; G01N 2015/1006; G01N 15/1429; G06T 7/0012;
(Continued)

(56) References Cited

U.S. PATENT DOCUMENTS

2017/0350805 A1* 12/2017 Murata ................... G01N 21/27
2019/0156947 A1* 5/2019 Nakamura ............ G16H 50/20
(Continued)

FOREIGN PATENT DOCUMENTS

| CN | 109461495 | 3/2019 |
| CN | 111492437 | 8/2020 |

OTHER PUBLICATIONS

Fiaschi, Luca. Learning based biological image analysis. Diss. 2014, pp. 1-97 (Year: 2014).*
(Continued)

*Primary Examiner* — Alex Kok S Liew
(74) *Attorney, Agent, or Firm* — ScienBiziP, P.C.

(57) ABSTRACT

A method for calculating a density of stem cells in a cell image and an electronic device are provided. A plurality of preset ratios and a plurality of density calculation models can be used to perform hierarchical density calculations on the cell image. Starting from the largest preset ratio (the first preset ratio) reduction of the cell image to no reduction, the density calculation is performed on the cell image using a model starting with a highest density calculation (the first density calculation model) to a model with the smallest density calculation (the third density calculation model), which can quickly detect densities of various stem cells. Using different preset ratios and corresponding density calculation models for calculation, it is not necessary to calculate the number of stem cells to obtain the density of stem cells, which improves a calculation efficiency of the density of stem cells.

20 Claims, 2 Drawing Sheets

(51) Int. Cl.
*G01N 33/483* (2006.01)
*G06T 7/00* (2017.01)

(52) U.S. Cl.
CPC .............. *G06T 2207/30024* (2013.01); *G06T 2207/30242* (2013.01)

(58) Field of Classification Search
CPC . G06T 2207/30024; G06T 2207/30242; G06T 2207/20081; G06T 3/4084; G06T 2207/10056; G06T 2207/10064; G06T 2207/30072; G06T 7/0016; G06T 2207/20084; G06T 2207/20212; G06T 2207/30168; G06T 5/50; G06T 5/70; G06T 7/0002; G06T 7/10; G06V 10/774; G06V 20/698; G06V 10/82; G06V 10/776; G06V 10/768; G06V 20/695; G06V 10/454; G06V 10/993; G06V 20/70; G06V 2201/03; G06F 18/214

See application file for complete search history.

(56) References Cited

U.S. PATENT DOCUMENTS

| | | | | |
|---|---|---|---|---|
| 2019/0228527 | A1* | 7/2019 | Ramirez | G06T 7/41 |
| 2020/0097701 | A1* | 3/2020 | Chukka | G06V 10/764 |
| 2021/0295960 | A1* | 9/2021 | Kalkstein | G16B 20/00 |
| 2021/0303818 | A1* | 9/2021 | Randolph | G06V 10/7715 |

OTHER PUBLICATIONS

Xue, Yao, et al. "Cell counting by regression using convolutional neural network." Computer Vision—ECCV 2016 Workshops: Amsterdam, The Netherlands, Oct. 8-10 and 15-16, 2016, Proceedings, Part I 14. Springer International Publishing, 2016, pp. 274-290. (Year: 2016).*

Chen, Hao, et al. "Mitosis detection in breast cancer histology images via deep cascaded networks." Proceedings of the AAAI conference on artificial intelligence. vol. 30. No. 1. 2016, pp. 1160-1166. (Year: 2016).*

Xie, Weidi, J. et al. "Microscopy cell counting and detection with fully convolutional regression networks." Computer methods in biomechanics and biomedical engineering: Imaging & Visualization 6.3 (2018), pp. 1-10 (Year: 2018).*

Guo, Yue, et al. "Sau-net: A universal deep network for cell counting." Proceedings of the 10th ACM international conference on bioinformatics, computational biology and health informatics, 2019, pp. 299-306 (Year: 2019).*

He, Shenghua, et al. "Automatic microscopic cell counting by use of deeply-supervised density regression model." Medical Imaging 2019: Digital Pathology. vol. 10956. SPIE, 2019, pp. 1-8. (Year: 2019).*

Zhang, Dongdong, et al. "Cell counting algorithm based on YOLOv3 and image density estimation." 2019 IEEE 4th international conference on signal and image processing (ICSIP). IEEE, 2019, pp. 920-924. (Year: 2019).*

Jiang, Ni, et al. "A cell counting framework based on random forest and density map." Applied sciences (Nov. 24, 2020), pp. 1-18 (Year: 2020).*

Ding, Xin, et al. "Classification Beats Regression: Counting of Cells from Greyscale Microscopic Images based on Annotation-free Training Samples." arXiv preprint arXiv:2010.14782 (Oct. 29, 2020), pp. 1-9 (Year: 2020).*

He, Shenghua, et al. "Deeply-Supervised Density Regression for Automatic Cell Counting in Microscopy Images." arXiv preprint arXiv:2011.03683 (Nov. 11, 2020), pp. 1-29. (Year: 2020).*

Shenghua He, Kyaw Thu Minn, Lilianna Solnica-Krezel, Mark Anastasio, and Hua Li "Automatic microscopic cell counting by use of deeply-supervised density regression model", Proc. SPIE 10956, Medical Imaging 2019: Digital Pathology, 109560L, Mar. 18, 2019 (Year: 2019).*

Shenghua He, Kyaw Thu Minn, Lilianna Solnica-Krezel, Mark A. Anastasio, Hua Li, Deeply-supervised density regression for automatic cell counting in microscopy images, Medical Image Analysis, vol. 68, 2021, 101892 (Year: 2021).*

* cited by examiner

METHOD FOR CALCULATING A DENSITY OF STEM CELLS IN A CELL IMAGE, ELECTRONIC DEVICE, AND STORAGE MEDIUM

FIELD

The present disclosure relates to a technical field of imaging, specifically a method for calculating a density of stem cells in a cell image, an electronic device, and a storage medium.

BACKGROUND

By calculating the number and volume of stem cells shown in an image, the actual density of stem cells can be calculated or estimated. However, known methods of calculating the number and volume of stem cells in the image may have lower efficiencies.

Therefore, a rapid estimation or calculation of the density of stem cells shown in an image is desirable.

DETAILED DESCRIPTION

The accompanying drawings combined with the detailed description illustrate the embodiments of the present disclosure hereinafter. It is noted that embodiments of the present disclosure and features of the embodiments can be combined when there is no conflict.

Various details are described in the following descriptions for a better understanding of the present disclosure, however, the present disclosure may also be implemented in other ways other than those described herein. The scope of the present disclosure is not to be limited by the specific embodiments disclosed below.

Unless defined otherwise, all technical and scientific terms used herein have the same meaning as commonly understood by one of ordinary skill in the art to which the present disclosure belongs. The terms used herein in the present disclosure are only for the purpose of describing specific embodiments and are not intended to limit the present disclosure.

Optionally, the method for calculating a density of stem cells in a cell image of the present disclosure is applied to one or more electronic devices. The electronic device includes hardware such as, but not limited to, a microprocessor and an Application Specific Integrated Circuit (ASIC), Field-Programmable Gate Array (FPGA), Digital Signal Processor (DSP), embedded devices, etc.

The electronic device may be a device such as a desktop computer, a notebook, a palmtop computer, or a cloud server. The electronic device can interact with users by using a keyboard, a mouse, a remote control, a touch panel, or a voice control device.

Figure 1:
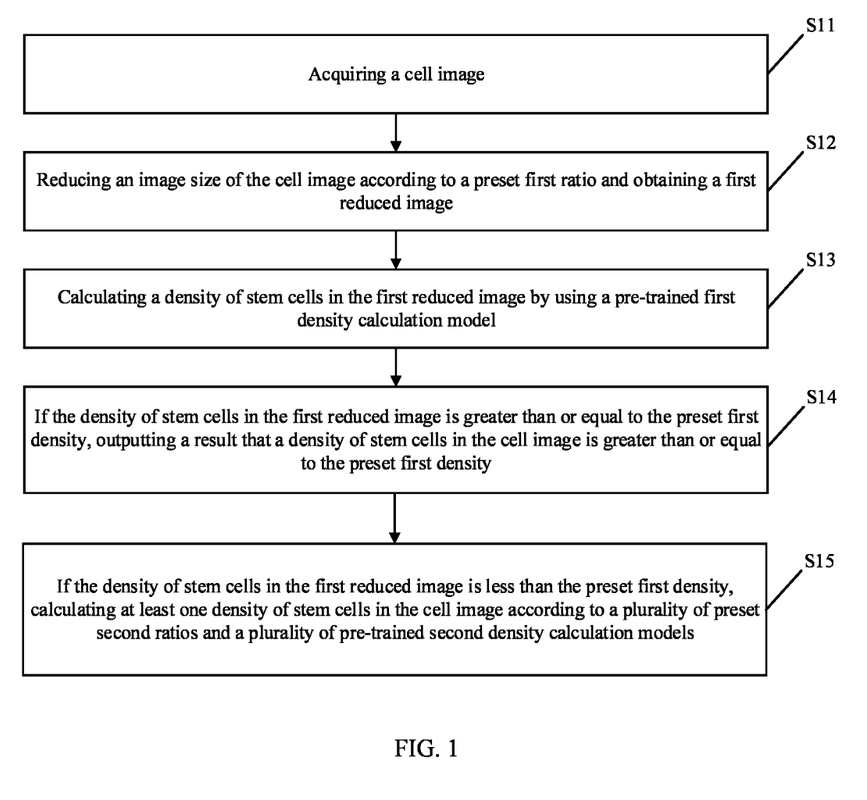
FIG. 1 shows a flowchart of a method for calculating a density of stem cells in a cell image provided in an embodiment of the present disclosure.

FIG. 1 is a flowchart of a method for calculating a density of stem cells in a cell image in an embodiment of the present disclosure. The method for calculating a density of stem cells in a cell image is applied to electronic devices. According to different needs, the order of the steps in the flowchart can be changed, and some can be omitted.

In block S11, acquiring a cell image.

The cell image refers to an image of cells that needs to be analyzed regarding a density of the stem cells shown in the cell image. The cells shown in the cell image may include, but is not limited to, stem cells, other cells, and impurities.

In some embodiments, before acquiring the cell image, the method further includes: acquiring a plurality of first training images; selecting, from the plurality of first training images, images with a density of stem cells greater than or equal to a preset first density as first positive sample images, and images with a density of stem cells less than the preset first density as first negative sample images; reducing image sizes of the first positive sample images and image sizes of the first negative sample images according to a preset first ratio; training and obtaining a first density calculation model with the reduced first positive sample images and the reduced first negative sample images.

The plurality of first training images are pre-collected images for training the first density calculation model. These first training images include cell images with different densities of stem cells. The images with a density of stem cells greater than or equal to the preset first density can be selected as the first positive sample images, and the images with a density of stem cells less than the preset first density can be selected as the first negative sample images. The preset first density may be 80%. Assuming that the preset first ratio is 60%, image sizes of the reduced first positive sample images and image sizes of the reduced first negative sample images are the first training images reduced by 60%. By training the reduced first positive sample images and the reduced first negative sample images, the first density calculation model is obtained. The first density calculation model can perform a density calculation on the cell image reduced by 60%.

In some embodiments, before acquiring the cell image, the method further includes: acquiring a plurality of second training images; for a target second ratio of the plurality of preset second ratios, selecting, from the plurality of second training images, images with a density of stem cells greater than or equal to a preset second density corresponding to the target second ratio as second positive sample images, and images with a density of stem cells less than the preset second density corresponding to the target second ratio as second negative sample images; reducing image sizes of the second positive sample images and image sizes of the second negative sample images according to the target second ratio; training and obtaining a second density calculation model corresponding to the target second ratio with the reduced second positive sample images and the reduced second negative sample images.

The plurality of second training images are pre-collected images for training the second density calculation models. Each second density calculation model corresponds to each preset second ratio. These second training images include cell images with different densities of stem cells. The images with a density of stem cells greater than or equal to each preset second density can be selected as the second positive sample images, and the images with a density of stem cells less than the each preset second density can be selected as the second negative sample images. Assuming that one preset second density is 60% and one preset second ratio corresponding to the one preset second density is 40%, image sizes of the reduced second positive sample images and image sizes of the reduced second negative sample images are the second training images reduced by 40%. By training the reduced second positive sample images and the reduced second negative sample images, the second density calculation model is obtained. The second density calculation model can perform a density calculation on the cell image reduced by 40%.

In some embodiments, before acquiring the cell image, the method further includes: acquiring a plurality of third training images; selecting, from the plurality of third training images, images with a density of stem cells greater than or equal to a preset third density as third positive sample images, and images with a density of stem cells less than the preset third density as third negative sample images; training and obtaining a third density calculation model with the reduced third positive sample images and the reduced third negative sample images.

The plurality of third training images are pre-collected images for training the third density calculation model. These third training images include cell images with different densities of stem cells. The images with a density of stem cells greater than or equal to the preset third density can be selected as the third positive sample images, and the images with a density of stem cells less than the preset third density can be selected as the third negative sample images. The preset third density may be 10%, for example. By training the reduced third positive sample images and the reduced third negative sample images, the third density calculation model is obtained. The third density calculation model can perform a density calculation on the cell image that has not been reduced.

In block S12, reducing an image size of the cell image according to a preset first ratio and obtaining a first reduced image.

In an embodiment of the present disclosure, the image size of the cell images may be reduced according to the preset first ratio to obtain the first reduced image. Assuming that the preset first ratio is 60%, the first reduced image is the cell images reduced by 60%. The size of the first reduced image is 40% of the size of the cell image.

In block S13, calculating a density of stem cells in the first reduced image by using a pre-trained first density calculation model.

The first density calculation model is used to calculate density of stem cells in the first reduced image. After calculating the density of stem cells in the first reduced image by using the pre-trained first density calculation model, the electronic device determines whether the density of stem cells in the first reduced image is greater than or equal to the preset first density. The preset first density may be a greater value, such as 80%. The density of stem cells in the first reduced image is greater than or equal to the preset first density (for example, 80%), or the density of stem cells in the first reduced image is less than the preset first density (for example, 80%).

In block S14, if the density of stem cells in the first reduced image is greater than or equal to the preset first density, outputting a result that a density of stem cells in the cell image is greater than or equal to the preset first density.

Assuming that the preset first density is 80%, if the density of stem cells in the first reduced image is greater than or equal to the preset first density, a text prompt or warning giving information that "a density of stem cells is greater than or equal to 80%" can be output.

In block S15, if the density of stem cells in the first reduced image is less than the preset first density, calculating at least one density of stem cells in the cell image according to a plurality of preset second ratios and a plurality of pre-trained second density calculation models.

The plurality of preset second ratios are set in advance. The plurality of preset second ratios are in one-to-one correspondence with the plurality of pre-trained second density calculation models. The preset first ratio is greater than each of the plurality of preset second ratios. For example, the preset first ratio may be 60%, and the plurality of preset second ratios may be 50%, 40%, 30%, 20%, and so on. The density of the plurality of pre-trained second density calculation models corresponding to the plurality of preset second ratios may be 60%, 50%, 40%, 30%, and so on.

In some embodiments, the method of calculating at least one density of stem cells in the cell image according to a plurality of preset second ratios and a plurality of pre-trained second density calculation models includes: obtaining a largest second ratio among the plurality of preset second ratios; reducing the image size of the cell image according to the largest second ratio and obtaining a second reduced image; calculating a density of stem cells in the second reduced image by using a pre-trained second density calculation model corresponding to the largest second ratio; when the density of stem cells in the second reduced image is less than a preset second density corresponding to the largest second ratio, obtaining a second largest second ratio among the plurality of preset second ratios; reducing the image size of the cell image according to the second largest second ratio and obtaining a third reduced image; calculating a density of stem cells in the third reduced image by using the pre-trained second density calculation model corresponding to the second largest second ratio.

Assuming that the plurality of preset second ratios are 50%, 40%, 30%, and 20%, a sorting result obtained by sorting the plurality of preset second ratios is 50%, 40%, 30%, and 20%. Among the plurality of preset second ratios, the largest second ratio is 50%, the second largest second ratio is 40%, the third largest second ratio is 30%, and the smallest second ratio is 20%.

First, the image size of the cell image can be reduced by 50% to obtain the second reduced image, and then the second reduced image can be input into a second density calculation model corresponding to the preset second ratio of 50%, thus the density of stem cells in the second reduced image can be obtained. The density of stem cells in the second reduced image can be less than a preset second density corresponding to the preset second ratio 50% or be greater than or equal to the preset second density corresponding to the largest second ratio 50%.

If the density of stem cells in the second reduced image is less the preset second density corresponding to the largest second ratio 50%, the image size of the cell image is reduced by 40% (the second largest second ratio is 40%) to obtain the third reduced image, and then the third reduced image can be input into a second density calculation model corresponding to the preset second ratio of 40%, thus the density of stem cells in the third reduced image can be obtained.

If the density of stem cells in the third reduced image is greater than or equal to a preset second density corresponding to the largest second ratio 40%, then according to the sorting result, the third largest second ratio among the plurality of preset second ratios is 30%, the image size of the cell image is reduced by 30%, and a second density calculation model corresponding to the preset second ratio of 30% is used to calculate a density of stem cells in the cell images reduced by 30%.

In some embodiments, if the density of stem cells in the second reduced image is greater than or equal to the preset second density corresponding to the largest second ratio, the method further includes: determining that the density of stem cells in the cell image is greater than or equal to the preset second density corresponding to the largest second ratio but less than the preset first density.

The preset first density is greater than each preset second density. Each preset second density is greater than the preset third density.

In the above embodiment, when the density of stem cells in the second reduced image is greater than or equal to the preset second density corresponding to the largest second ratio, because the preset first density is greater than each preset second density, it indicates that a density of stem cells in the second reduced image is greater than or equal to the preset second density corresponding to the largest second ratio, but less than the preset first density.

When it is determined that the density of stem cells in the cell image is greater than or equal to the preset second density corresponding to the largest second ratio, but less than the preset first density, the calculation of the density of the stem cell in the cell image ends.

In some embodiments, if the at least one density of stem cells in the cell image is less than the preset second density, the method further includes: calculating a density of stem cells in the cell image by using the pre-trained third density calculation model.

The preset third density, in comparison with the preset first density and each preset second density, is a relatively small density, such as 10%.

When it is determined that the at least one density of stem cells in the second reduced image is less than the preset second density, the cell image do not need to be reduced at this time, and the cell image is directly input into the third density calculation model. An output result of the third density calculation model may be that the density of stem cells in the cell image is less than the preset third density (for example, 10%), or that the density of stem cells in the cell image is greater than or equal to the preset third density (for example, 10%) but less than the preset second density (for example, 20%).

The preset first ratio, each preset second ratio, and the preset third ratio are all values greater than 0 and less than 1.

In the method provided by the embodiment of the present disclosure, a plurality of preset ratios and a plurality of density calculation models can be used to perform hierarchical density calculations on the cell image. Starting from the largest preset ratio (the first preset ratio) reduction of the cell image to no reduction, the density calculation is performed on the cell image using a model starting with a highest density calculation (the first density calculation model) to a model with the smallest density calculation (the third density calculation model), which can quickly detect densities of various stem cells. For the reduced images, those with a higher density of stem cells are easy to be detected, and those with a lower density of stem cells are not easy to be detected. Using different preset ratios and corresponding density calculation models for calculation, it is not necessary to calculate the number of stem cells to obtain the density of stem cells, which improves a calculation efficiency of the density of stem cells.

Figure 2:
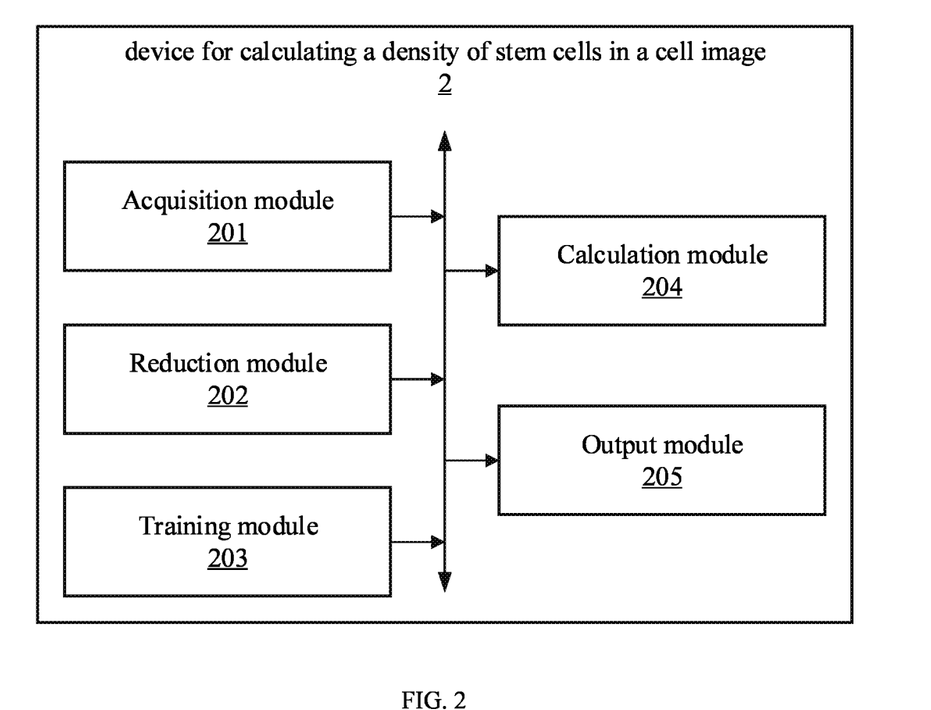
FIG. 2 shows a schematic structural diagram of a device for calculating a density of stem cells in a cell image provided in an embodiment of the present disclosure.

FIG. 2 shows a schematic structural diagram of a device for calculating a density of stem cells in a cell image provided in the embodiment of the present disclosure.

In some embodiments, the device for calculating a density of stem cells in a cell image 2 runs in an electronic device. The device for calculating a density of stem cells in a cell image 2 can include a plurality of function modules consisting of program code segments. The program code of each program code segments in the device for calculating a density of stem cells in a cell image 2 can be stored in a memory and executed by at least one processor to perform image processing (described in detail in FIG. 2).

As shown in FIG. 2, the device for calculating a density of stem cells in a cell image 2 can include: an acquisition module 201, a reduction module 202, a training module 203, a calculation module 204, and an output module 205. A module as referred to in the present disclosure refers to a series of computer-readable instruction segments that can be executed by at least one processor and that are capable of performing fixed functions, which are stored in a memory. In some embodiment, the functions of each module will be detailed.

The above-mentioned integrated unit implemented in a form of software functional modules can be stored in a non-transitory readable storage medium. The above software function modules are stored in a storage medium and includes several instructions for causing an electronic device (which can be a personal computer, a dual-screen device, or a network device) or a processor to execute the method described in various embodiments in the present disclosure.

The acquisition module 201 acquires a cell image.

The cell image refers to an image of cells that needs to be analyzed regarding a density of the stem cells shown in the cell image. The cells shown in the cell image may include, but is not limited to, stem cells, other cells, and impurities.

In some embodiments, before acquiring the cell image, the acquisition module 201 acquires a plurality of first training images. The acquisition module 201, selects, from the plurality of first training images, images with a density of stem cells greater than or equal to a preset first density as first positive sample images, and images with a density of stem cells less than the preset first density as first negative sample images. The reduction module 202 reduces image sizes of the first positive sample images and image sizes of the first negative sample images according to a preset first ratio. The training module 203 trains and obtains a first density calculation model with the reduced first positive sample images and the reduced first negative sample images.

The plurality of first training images are pre-collected images for training the first density calculation model. These first training images include cell images with different densities of stem cells. The images with a density of stem cells greater than or equal to the preset first density can be selected as the first positive sample images, and the images with a density of stem cells less than the preset first density can be selected as the first negative sample images. The preset first density may be 80%. Assuming that the preset first ratio is 60%, image sizes of the reduced first positive sample images and image sizes of the reduced first negative sample images are the first training images reduced by 60%. By training the reduced first positive sample images and the reduced first negative sample images, the first density calculation model is obtained. The first density calculation model can perform a density calculation on the cell image reduced by 60%.

In some embodiments, before acquiring the cell image, the acquisition module 201 acquires a plurality of second training images. For a target second ratio of the plurality of preset second ratios, the acquisition module 201, selects, from the plurality of second training images, images with a density of stem cells greater than or equal to a preset second density corresponding to the target second ratio as second positive sample images, and images with a density of stem cells less than the preset second density corresponding to the target second ratio as second negative sample images. The reduction module 202 reduces image sizes of the second positive sample images and image sizes of the second negative sample images according to the target second ratio. The training module 203 trains and obtains a second density calculation model corresponding to the target second ratio with the reduced second positive sample images and the reduced second negative sample images.

The plurality of second training images are pre-collected images for training the second density calculation models. Each second density calculation model corresponds to each preset second ratio. These second training images include cell images with different densities of stem cells. The images with a density of stem cells greater than or equal to each preset second density can be selected as the second positive sample images, and the images with a density of stem cells less than the each preset second density can be selected as the second negative sample images. Assuming that one preset second density is 60% and one preset second ratio corresponding to the one preset second density is 40%, image sizes of the reduced second positive sample images and image sizes of the reduced second negative sample images are the second training images reduced by 40%. By training the reduced second positive sample images and the reduced second negative sample images, the second density calculation model is obtained. The second density calculation model can perform a density calculation on the cell image reduced by 40%.

In some embodiments, before acquiring the cell image, the acquisition module 201 acquires a plurality of third training images. The acquisition module 201, selects, from the plurality of third training images, images with a density of stem cells greater than or equal to a preset third density as third positive sample images, and images with a density of stem cells less than the preset third density as third negative sample images. The training module 203 trains and obtains a third density calculation model with the reduced third positive sample images and the reduced third negative sample images.

The plurality of third training images are pre-collected images for training the third density calculation model. These third training images include cell images with different densities of stem cells. The images with a density of stem cells greater than or equal to the preset third density can be selected as the third positive sample images, and the images with a density of stem cells less than the preset third density can be selected as the third negative sample images. The preset third density may be 10%, for example. By training the reduced third positive sample images and the reduced third negative sample images, the third density calculation model is obtained. The third density calculation model can perform a density calculation on the cell image that has not been reduced.

The reduction module 202 reduces an image size of the cell image according to a preset first ratio and obtaining a first reduced image.

In an embodiment of the present disclosure, the image size of the cell images may be reduced according to the preset first ratio to obtain the first reduced image. Assuming that the preset first ratio is 60%, the first reduced image is the cell images reduced by 60%. The size of the first reduced image is 40% of the size of the cell image.

The calculation module 204 calculates a density of stem cells in the first reduced image by using a pre-trained first density calculation model.

The first density calculation model is used to calculate density of stem cells in the first reduced image. After calculating the density of stem cells in the first reduced image by using the pre-trained first density calculation model, the electronic device determines whether the density of stem cells in the first reduced image is greater than or equal to the preset first density. The preset first density may be a greater value, such as 80%. The density of stem cells in the first reduced image is greater than or equal to the preset first density (for example, 80%), or the density of stem cells in the first reduced image is less than the preset first density (for example, 80%).

The output module 205, if the density of stem cells in the first reduced image is greater than or equal to the preset first density, outputs a result that a density of stem cells in the cell image is greater than or equal to the preset first density.

Assuming that the preset first density is 80%, if the density of stem cells in the first reduced image is greater than or equal to the preset first density, a text prompt or warning giving information that "a density of stem cells is greater than or equal to 80%" can be output.

If the density of stem cells in the first reduced image is less than the preset first density, the calculation module 204 calculates at least one density of stem cells in the cell image according to a plurality of preset second ratios and a plurality of pre-trained second density calculation models.

The plurality of preset second ratios are set in advance. The plurality of preset second ratios are in one-to-one correspondence with the plurality of pre-trained second density calculation models. The preset first ratio is greater than each of the plurality of preset second ratios. For example, the preset first ratio may be 60%, and the plurality of preset second ratios may be 50%, 40%, 30%, 20%, and so on. The density of the plurality of pre-trained second density calculation models corresponding to the plurality of preset second ratios may be 60%, 50%, 40%, 30%, and so on.

In some embodiments, the method of calculating at least one density of stem cells in the cell image according to a plurality of preset second ratios and a plurality of pre-trained second density calculation models includes: obtaining a largest second ratio among the plurality of preset second ratios; reducing the image size of the cell image according to the largest second ratio and obtaining a second reduced image; calculating a density of stem cells in the second reduced image by using a pre-trained second density calculation model corresponding to the largest second ratio; when the density of stem cells in the second reduced image is less than a preset second density corresponding to the largest second ratio, obtaining a second largest second ratio among the plurality of preset second ratios; reducing the image size of the cell image according to the second largest second ratio and obtaining a third reduced image; calculating a density of stem cells in the third reduced image by using the pre-trained second density calculation model corresponding to the second largest second ratio.

Assuming that the plurality of preset second ratios are 50%, 40%, 30%, and 20%, a sorting result obtained by sorting the plurality of preset second ratios is 50%, 40%, 30%, and 20%. Among the plurality of preset second ratios, the largest second ratio is 50%, the second largest second ratio is 40%, the third largest second ratio is 30%, and the smallest second ratio is 20%.

First, the image size of the cell image can be reduced by 50% to obtain the second reduced image, and then the second reduced image can be input into a second density calculation model corresponding to the preset second ratio of 50%, thus the density of stem cells in the second reduced image can be obtained. The density of stem cells in the second reduced image can be less than a preset second density corresponding to the preset second ratio 50% or be greater than or equal to the preset second density corresponding to the largest second ratio 50%.

If the density of stem cells in the second reduced image is less the preset second density corresponding to the largest second ratio 50%, the image size of the cell image is reduced by 40% (the second largest second ratio is 40%) to obtain the third reduced image, and then the third reduced image can be input into a second density calculation model corresponding to the preset second ratio of 40%, thus the density of stem cells in the third reduced image can be obtained.

If the density of stem cells in the third reduced image is greater than or equal to a preset second density corresponding to the largest second ratio 40%, then according to the sorting result, the third largest second ratio among the plurality of preset second ratios is 30%, the image size of the cell image is reduced by 30%, and a second density calculation model corresponding to the preset second ratio of 30% is used to calculate a density of stem cells in the cell images reduced by 30%.

In some embodiments, if the density of stem cells in the second reduced image is greater than or equal to the preset second density corresponding to the largest second ratio, the output module 205 determines that the density of stem cells in the cell image is greater than or equal to the preset second density corresponding to the largest second ratio but less than the preset first density.

The preset first density is greater than each preset second density. Each preset second density is greater than the preset third density.

In the above embodiment, when the density of stem cells in the second reduced image is greater than or equal to the preset second density corresponding to the largest second ratio, because the preset first density is greater than each preset second density, it indicates that a density of stem cells in the second reduced image is greater than or equal to the preset second density corresponding to the largest second ratio, but less than the preset first density.

When it is determined that the density of stem cells in the cell image is greater than or equal to the preset second density corresponding to the largest second ratio, but less than the preset first density, the calculation of the density of the stem cell in the cell image ends.

In some embodiments, if the at least one density of stem cells in the cell image is less than the preset second density, the method further includes: calculating a density of stem cells in the cell image by using the pre-trained third density calculation model.

The preset third density, in comparison with the preset first density and each preset second density, is a relatively small density, such as 10%.

When it is determined that the at least one density of stem cells in the second reduced image is less than the preset second density, the cell image do not need to be reduced at this time, and the cell image is directly input into the third density calculation model. An output result of the third density calculation model may be that the density of stem cells in the cell image is less than the preset third density (for example, 10%), or that the density of stem cells in the cell image is greater than or equal to the preset third density (for example, 10%) but less than the preset second density (for example, 20%).

The preset first ratio, each preset second ratio, and the preset third ratio are all values greater than 0 and less than 1.

In the device provided by the embodiment of the present disclosure, a plurality of preset ratios and a plurality of density calculation models can be used to perform hierarchical density calculations on the cell image. Starting from the largest preset ratio (the first preset ratio) reduction of the cell image to no reduction, the density calculation is performed on the cell image using a model starting with a highest density calculation (the first density calculation model) to a model with the smallest density calculation (the third density calculation model), which can quickly detect densities of various stem cells. For the reduced images, those with a higher density of stem cells are easy to be detected, and those with a lower density of stem cells are not easy to be detected. Using different preset ratios and corresponding density calculation models for calculation, it is not necessary to calculate the number of stem cells to obtain the density of stem cells, which improves a calculation efficiency of the density of stem cells.

The embodiment also provides a non-transitory readable storage medium having computer-readable instructions stored therein. The computer-readable instructions are executed by a processor to implement the steps in the above-mentioned method for calculating a density of stem cells in a cell image, such as in steps in blocks S11-S15 shown in FIG. 1:

In block S11: acquiring a cell image;

In block S12: reducing an image size of the cell image according to a preset first ratio and obtaining a first reduced image;

In block S13: calculating a density of stem cells in the first reduced image by using a pre-trained first density calculation model;

In block S14, if the density of stem cells in the first reduced image is greater than or equal to the preset first density, outputting a result that a density of stem cells in the cell image is greater than or equal to the preset first density;

In block S15: if the density of stem cells in the first reduced image is less than the preset first density, calculating at least one density of stem cells in the cell image according to a plurality of preset second ratios and a plurality of pre-trained second density calculation models.

The computer-readable instructions are executed by the processor to realize the functions of each module/unit in the above-mentioned device embodiments, such as the modules 201-205 in FIG. 2.

Figure 3:
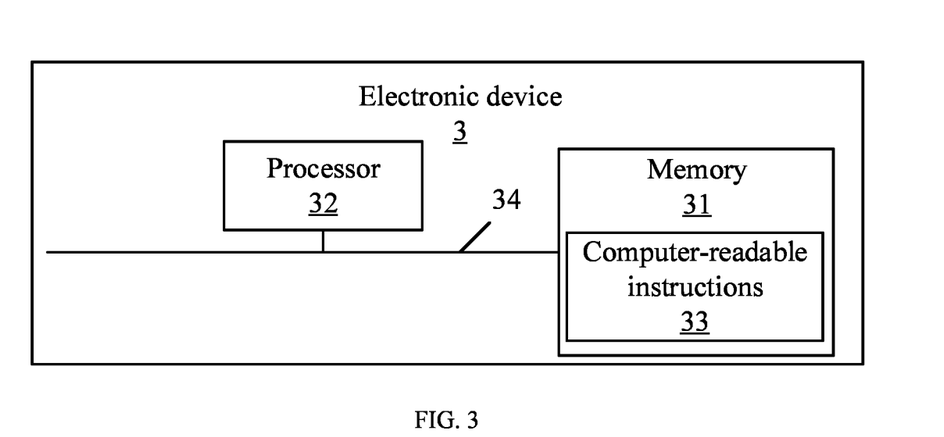
FIG. 3 shows a schematic structural diagram of an electronic device provided in an embodiment of the present disclosure.

FIG. 3 is a schematic structural diagram of an electronic device provided in an embodiment of the present disclosure. The electronic device 3 may include: a memory 31, at least one processor 32, and computer-readable instructions 33 stored in the memory 31 and executable on the at least one processor 32, for example, image recognition programs. memory 31 and the at least one processor 32 connected by at least one communication bus 34. The processor 32 executes the computer-readable instructions to implement the steps in the embodiment of the method for calculating a density of stem cells in a cell image, such as in steps in block S11-S15 shown in FIG. 1. Alternatively, the processor 32 executes the computer-readable instructions to implement the functions of the modules/units in the foregoing device embodiments, such as the modules 201-205 in FIG. 2.

For example, the computer-readable instructions can be divided into one or more modules/units, and the one or more modules/units are stored in the memory 31 and executed by the at least one processor 32. The one or more modules/units can be a series of computer-readable instruction segments capable of performing specific functions, and the instruction segments are used to describe execution processes of the computer-readable instructions in the electronic device 3. For example, the computer-readable instruction can be divided into the acquisition module 201, the reduction module 202, the training module 203, the calculation module 204, and the output module 205 as in FIG. 2.

The electronic device 3 can be an electronic device such as a desktop computer, a notebook, a palmtop computer, and a cloud server. Those skilled in the art will understand that the schematic diagram 3 is only an example of the electronic device 3 and does not constitute a limitation on the electronic device 3. Another electronic device 3 may include more or fewer components than shown in the figures or may combine some components or have different components. For example, the electronic device 3 may further include an input/output device, a network access device, a bus, and the like.

The at least one processor 32 can be a central processing unit (CPU), or can be another general-purpose processor, digital signal processor (DSPs), application-specific integrated circuit (ASIC), Field-Programmable Gate Array (FPGA), another programmable logic device, discrete gate, transistor logic device, or discrete hardware component, etc. The processor 32 can be a microprocessor or any conventional processor. The processor 32 is a control center of the electronic device 3 and connects various parts of the entire electronic device 3 by using various interfaces and lines.

The memory 31 can be configured to store the computer-readable instructions and/or modules/units. The processor 32 may run or execute the computer-readable instructions 33 and/or modules/units stored in the memory 31 and may call up data stored in the memory 31 to implement various functions of the electronic device 3. The memory 31 mainly includes a storage program area and a storage data area. The storage program area may store an operating system, and an application program required for at least one function (such as a sound playback function, an image playback function, etc.), etc. The storage data area may store data (such as audio data, phone book data, etc.) created according to the use of the electronic device 3. In addition, the memory 31 may include a high-speed random access memory, and may also include a non-transitory storage medium, such as a hard disk, an internal memory, a plug-in hard disk, a smart media card (SMC), a secure digital (SD) Card, a flashcard, at least one disk storage device, a flash memory device, or another non-transitory solid-state storage device.

When the modules/units integrated into the electronic device 3 are implemented in the form of software functional units having been sold or used as independent products, they can be stored in a non-transitory readable storage medium. Based on this understanding, all or part of the processes in the methods of the above embodiments implemented by the present disclosure can also be completed by related hardware instructed by computer-readable instructions. The computer-readable instructions can be stored in a non-transitory readable storage medium. The computer-readable instructions, when executed by the processor, may implement the steps of the foregoing method embodiments. The computer-readable instructions include computer-readable instruction codes, and the computer-readable instruction codes can be in a source code form, an object code form, an executable file, or some intermediate form. The non-transitory readable storage medium can include any entity or device capable of carrying the computer-readable instruction code, such as a recording medium, a U disk, a mobile hard disk, a magnetic disk, an optical disk, a computer memory, or a read-only memory (ROM).

In the several embodiments provided in the preset application, the disclosed electronic device and method can be implemented in other ways. For example, the embodiments of the devices described above are merely illustrative. For example, divisions of the units are only logical function divisions, and there can be other manners of division in actual implementation.

In addition, each functional unit in each embodiment of the present disclosure can be integrated into one processing unit, or can be physically present separately in each unit or two or more units can be integrated into one unit. The above modules can be implemented in a form of hardware or in a form of a software functional unit.

The present disclosure is not limited to the details of the above-described exemplary embodiments, and the present disclosure can be embodied in other specific forms without departing from the spirit or essential characteristics of the present disclosure. Therefore, the present embodiments are to be considered as illustrative and not restrictive, and the scope of the present disclosure is defined by the appended claims. All changes and variations in the meaning and scope of equivalent elements are included in the present disclosure. Any reference sign in the claims should not be construed as limiting the claim. Furthermore, the word "comprising" does not exclude other units nor does the singular exclude the plural. A plurality of units or devices stated in the system claims may also be implemented by one unit or device by using software or hardware. Words such as "first" and "second" are used to indicate names, but not in any particular order.

Finally, the above embodiments are only used to illustrate technical solutions of the present disclosure and are not to be taken as restrictions on the technical solutions. Although the present disclosure has been described in detail with reference to the above embodiments, those skilled in the art should understand that the technical solutions described in one embodiment can be modified, or some of the technical features can be equivalently substituted, and that these modifications or substitutions are not to detract from the essence of the technical solutions or from the scope of the technical solutions of the embodiments of the present disclosure.

What is claimed is:

1. A method for calculating a density of stem cells in a cell image, the method comprising:
   acquiring a cell image;
   reducing an image size of the cell image according to a preset first ratio and obtaining a first reduced image;
   calculating a density of stem cells in the first reduced image by using a pre-trained first density calculation model; and
   when the density of stem cells in the first reduced image is less than a preset first density, calculating at least one density of stem cells in the cell image according to a plurality of preset second ratios and a plurality of pre-trained second density calculation models, wherein the plurality of preset second ratios are in one-to-one correspondence with the plurality of pre-trained second density calculation models.

2. The method for calculating a density of stem cells in a cell image of claim 1, the method further comprising:

when the at least one density of stem cells in the cell image is less than a preset second density, calculating a density of stem cells in the cell image by using a pre-trained third density calculation model.

3. The method for calculating a density of stem cells in a cell image of claim 1, wherein calculating at least one density of stem cells in the cell image according to a plurality of preset second ratios and a plurality of pre-trained second density calculation models comprises:
obtaining a largest second ratio among the plurality of preset second ratios;
reducing the image size of the cell image according to the largest second ratio and obtaining a second reduced image;
calculating a density of stem cells in the second reduced image by using a pre-trained second density calculation model corresponding to the largest second ratio;
when the density of stem cells in the second reduced image is less than a preset second density corresponding to the largest second ratio, obtaining a second largest second ratio among the plurality of preset second ratios;
reducing the image size of the cell image according to the second largest second ratio and obtaining a third reduced image; and
calculating a density of stem cells in the third reduced image by using a pre-trained second density calculation model corresponding to the second largest second ratio.

4. The method for calculating a density of stem cells in a cell image of claim 3, the method further comprising:
if the density of stem cells in the second reduced image is greater than or equal to the preset second density corresponding to the largest second ratio, determining that the density of stem cells in the cell image is greater than or equal to the preset second density corresponding to the largest second ratio but less than the preset first density.

5. The method for calculating a density of stem cells in a cell image of claim 4, before acquiring the cell image, the method further comprising:
acquiring a plurality of first training images;
selecting, from the plurality of first training images, images with a density of stem cells greater than or equal to the preset first density as first positive sample images, and images with a density of stem cells less than the preset first density as first negative sample images;
reducing image sizes of the first positive sample images and image sizes of the first negative sample images according to the preset first ratio; and
training and obtaining the first density calculation model with the reduced first positive sample images and the reduced first negative sample images.

6. The method for calculating a density of stem cells in a cell image of claim 5, before acquiring the cell image, the method further comprising:
acquiring a plurality of second training images;
for a target second ratio of the plurality of preset second ratios, selecting, from the plurality of second training images, images with a density of stem cells greater than or equal to a preset second density corresponding to the target second ratio as second positive sample images, and images with a density of stem cells less than the preset second density corresponding to the target second ratio as second negative sample images;
reducing image sizes of the second positive sample images and image sizes of the second negative sample images according to the target second ratio; and
training and obtaining a second density calculation model corresponding to the target second ratio with the reduced second positive sample images and the reduced second negative sample images.

7. The method for calculating a density of stem cells in a cell image of claim 6, before acquiring the cell image, the method further comprising:
acquiring a plurality of third training images;
selecting, from the plurality of third training images, images with a density of stem cells greater than or equal to a preset third density as third positive sample images, and images with a density of stem cells less than the preset third density as third negative sample images;
training and obtaining the third density calculation model with the reduced third positive sample images and the reduced third negative sample images.

8. A electronic device comprising a memory and a processor, the memory stores at least one computer-readable instruction, and the processor executes the at least one computer-readable instruction to:
acquire a cell image;
reduce an image size of the cell image according to a preset first ratio and obtain a first reduced image;
calculate a density of stem cells in the first reduced image by using a pre-trained first density calculation model; and
when the density of stem cells in the first reduced image is less than a preset first density, calculate at least one density of stem cells in the cell image according to a plurality of preset second ratios and a plurality of pre-trained second density calculation models, wherein the plurality of preset second ratios are in one-to-one correspondence with the plurality of pre-trained second density calculation models.

9. The electronic device of claim 8, wherein the processor further to:
when the at least one density of stem cells in the cell image is less than a preset second density, calculate a density of stem cells in the cell image by using a pre-trained third density calculation model.

10. The electronic device of claim 8, wherein calculating at least one density of stem cells in the cell image according to a plurality of preset second ratios and a plurality of pre-trained second density calculation models comprises:
obtaining a largest second ratio among the plurality of preset second ratios;
reducing the image size of the cell image according to the largest second ratio and obtaining a second reduced image;
calculating a density of stem cells in the second reduced image by using a pre-trained second density calculation model corresponding to the largest second ratio;
when the density of stem cells in the second reduced image is less than a preset second density corresponding to the largest second ratio, obtaining a second largest second ratio among the plurality of preset second ratios;
reducing the image size of the cell image according to the second largest second ratio and obtaining a third reduced image; and
calculating a density of stem cells in the third reduced image by using a pre-trained second density calculation model corresponding to the second largest second ratio.

11. The electronic device of claim 10, wherein the processor further to:
  if the density of stem cells in the second reduced image is greater than or equal to the preset second density corresponding to the largest second ratio, determining that the density of stem cells in the cell image is greater than or equal to the preset second density corresponding to the largest second ratio but less than the preset first density.

12. The electronic device of claim 11, before acquiring the cell image, wherein the processor further to:
  acquire a plurality of first training images;
  select, from the plurality of first training images, images with a density of stem cells greater than or equal to the preset first density as first positive sample images, and images with a density of stem cells less than the preset first density as first negative sample images;
  reduce image sizes of the first positive sample images and image sizes of the first negative sample images according to the preset first ratio; and
  train and obtain the first density calculation model with the reduced first positive sample images and the reduced first negative sample images.

13. The electronic device of claim 12, before acquiring the cell image, the processor further to:
  acquire a plurality of second training images;
  for a target second ratio of the plurality of preset second ratios, select, from the plurality of second training images, images with a density of stem cells greater than or equal to a preset second density corresponding to the target second ratio as second positive sample images, and images with a density of stem cells less than the preset second density corresponding to the target second ratio as second negative sample images;
  reduce image sizes of the second positive sample images and image sizes of the second negative sample images according to the target second ratio; and
  train and obtain a second density calculation model corresponding to the target second ratio with the reduced second positive sample images and the reduced second negative sample images.

14. The electronic device of claim 13, before acquiring the cell image, wherein the processor further to:
  acquire a plurality of third training images;
  select, from the plurality of third training images, images with a density of stem cells greater than or equal to a preset third density as third positive sample images, and images with a density of stem cells less than the preset third density as third negative sample images; and
  train and obtain the third density calculation model with the reduced third positive sample images and the reduced third negative sample images.

15. A non-transitory storage medium having stored thereon at least one computer-readable instructions that, when the at least one computer-readable instructions are executed by a processor to implement the following method:
  acquiring a cell image;
  reducing an image size of the cell image according to a preset first ratio and obtaining a first reduced image;
  calculating a density of stem cells in the first reduced image by using a pre-trained first density calculation model; and
  when the density of stem cells in the first reduced image is less than a preset first density, calculating at least one density of stem cells in the cell image according to a plurality of preset second ratios and a plurality of pre-trained second density calculation models, wherein the plurality of preset second ratios are in one-to-one correspondence with the plurality of pre-trained second density calculation models.

16. The non-transitory storage medium according to claim 15, the method further comprising:
  when the at least one density of stem cells in the cell image is less than a preset second density, calculating a density of stem cells in the cell image by using a pre-trained third density calculation model.

17. The non-transitory storage medium of claim 15, wherein calculating at least one density of stem cells in the cell image according to a plurality of preset second ratios and a plurality of pre-trained second density calculation models comprises:
  obtaining a largest second ratio among the plurality of preset second ratios;
  reducing the image size of the cell image according to the largest second ratio and obtaining a second reduced image;
  calculating a density of stem cells in the second reduced image by using a pre-trained second density calculation model corresponding to the largest second ratio;
  when the density of stem cells in the second reduced image is less than a preset second density corresponding to the largest second ratio, obtaining a second largest second ratio among the plurality of preset second ratios;
  reducing the image size of the cell image according to the second largest second ratio and obtaining a third reduced image; and
  calculating a density of stem cells in the third reduced image by using a pre-trained second density calculation model corresponding to the second largest second ratio.

18. The non-transitory storage medium of claim 17, the method further comprising:
  if the density of stem cells in the second reduced image is greater than or equal to the preset second density corresponding to the largest second ratio, determining that the density of stem cells in the cell image is greater than or equal to the preset second density corresponding to the largest second ratio but less than the preset first density.

19. The non-transitory storage medium of claim 18, before acquiring the cell image, the method further comprising:
  acquiring a plurality of first training images;
  selecting, from the plurality of first training images, images with a density of stem cells greater than or equal to the preset first density as first positive sample images, and images with a density of stem cells less than the preset first density as first negative sample images;
  reducing image sizes of the first positive sample images and image sizes of the first negative sample images according to the preset first ratio; and
  training and obtaining the first density calculation model with the reduced first positive sample images and the reduced first negative sample images.

20. The non-transitory storage medium of claim 19, before acquiring the cell image, the method further comprising:
  acquiring a plurality of second training images;
  for a target second ratio of the plurality of preset second ratios, selecting, from the plurality of second training images, images with a density of stem cells greater than or equal to a preset second density corresponding to the target second ratio as second positive sample images, and images with a density of stem cells less than the preset second density corresponding to the target second ratio as second negative sample images;

reducing image sizes of the second positive sample images and image sizes of the second negative sample images according to the target second ratio; and training and obtaining a second density calculation model corresponding to the target second ratio with the reduced second positive sample images and the reduced second negative sample images.

\* \* \* \* \*